(12) United States Patent
Mizuno

(10) Patent No.: US 11,896,010 B2
(45) Date of Patent: Feb. 13, 2024

(54) URACIL COMPOUND AND USE THEREOF

(71) Applicant: Sumitomo Chemical Company, Limited, Tokyo (JP)

(72) Inventor: Hajime Mizuno, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 604 days.

(21) Appl. No.: 17/257,973

(22) PCT Filed: Jul. 11, 2019

(86) PCT No.: PCT/JP2019/027510
§ 371 (c)(1),
(2) Date: Jan. 5, 2021

(87) PCT Pub. No.: WO2020/013279
PCT Pub. Date: Jan. 16, 2020

(65) Prior Publication Data
US 2021/0153505 A1    May 27, 2021

(30) Foreign Application Priority Data
Jul. 12, 2018   (JP) ................. 2018-132119

(51) Int. Cl.
*A01N 43/54*   (2006.01)
*C07D 401/14*  (2006.01)

(52) U.S. Cl.
CPC ........... *A01N 43/54* (2013.01); *C07D 401/14* (2013.01)

(58) Field of Classification Search
CPC .............................. A01N 43/54; C07D 401/14
See application file for complete search history.

(56) References Cited

U.S. PATENT DOCUMENTS

| | | | |
|---|---|---|---|
| 6,187,716 B1 | 2/2001 | Andree et al. | |
| 6,537,948 B1 | 3/2003 | Tohyama et al. | |
| 2004/0138063 A1 | 7/2004 | Mito | |
| 2004/0254077 A1 | 12/2004 | Tohyama et al. | |

FOREIGN PATENT DOCUMENTS

| | | |
|---|---|---|
| JP | 2001506245 A | 5/2001 |
| JP | 2002155061 A | 5/2002 |
| WO | 02098228 A1 | 12/2002 |
| WO | 2003014109 A1 | 2/2003 |

OTHER PUBLICATIONS

Examination Report dated May 13, 2022 in IN Application No. 202147000655.
English Translation of International Preliminary Report on Patentability dated Jan. 12, 2021 in International Application No. PCT/JP2019/027510.
English Translation of International Search Report dated Sep. 3, 2019 in International Application No. PCT/JP2019/027510.

*Primary Examiner* — Robert A Wax
*Assistant Examiner* — John Seungjai Kwon
(74) *Attorney, Agent, or Firm* — Panitch Schwarze Belisario & Nadel LLP

(57) ABSTRACT

A compound having excellent weed control efficacy and high safety against useful plants is represented by formula (A):

(A)

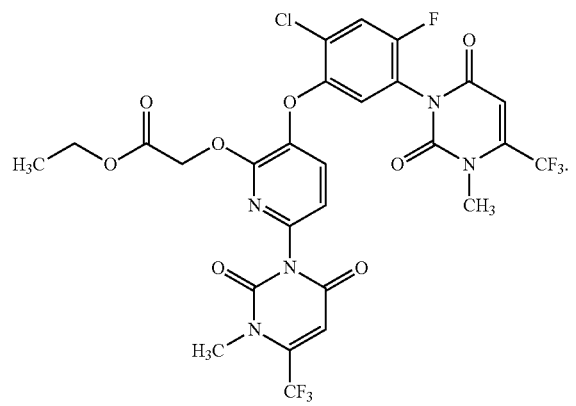

3 Claims, No Drawings

URACIL COMPOUND AND USE THEREOF

CROSS-REFERENCE TO RELATED APPLICATIONS

This application is a Section 371 of International Application No. PCT/JP2019/027510, filed Jul. 11, 2019, which was published in the Japanese language on Jan. 16, 2020 under International Publication No. WO 2020/013279 A1, which claims priority under 35 U.S.C. § 119(b) to Japanese Application No. 2018-132119, filed on Jul. 12, 2018, the disclosures of which are incorporated herein by reference in their entireties.

TECHNICAL FIELD

The present invention relates to a uracil compound and use thereof.

BACKGROUND ART

Patent Document 1 discloses that a compound represented by formula (B)

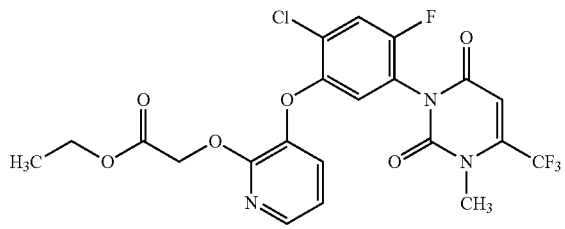

(B)

(hereinafter referred to as "Compound B") has weed control efficacies.

CITATION LIST

Patent Document

[Patent Document 1] U.S. Pat. No. 6,537,948 B1

SUMMARY OF INVENTION

Technical Problem

An object of the present invention is to provide a compound having excellent weed control efficacies and high safety against useful plants.

Solution to Problem

The present invention provides the followings.
[1] A compound represented by formula (A)

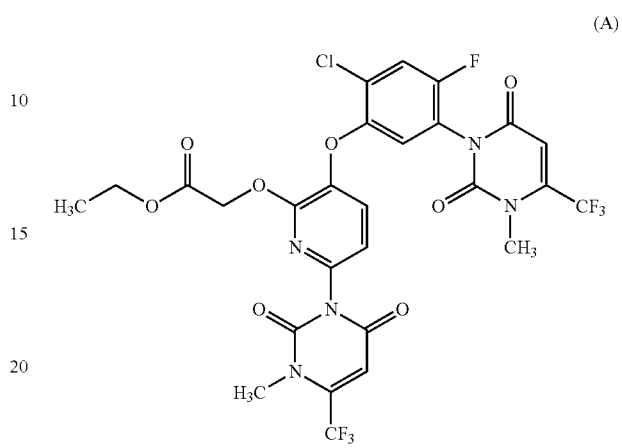

(A)

(hereinafter referred to as "Compound A").
[2] A herbicidal composition comprising the compound according to [1] and an inert carrier (hereinafter referred to as "Composition A").
[3] A method for controlling a weed which comprises applying the compound according to [1] to a weed or a habitat where a weed lives.

Advantageous Effects of Invention

The Compound A has excellent weed control efficacies and high safety against useful plants, and thus is useful as an active ingredient of a herbicidal composition.

DESCRIPTION OF EMBODIMENTS

The Composition A comprises the Compound A and an inert carrier. The Composition A is usually prepared by mixing the Compound A with an inert carrier such as a solid carrier and a liquid carrier, and if necessary, adding surfactant(s) and other auxiliary agent(s) for formulation to formulate into a wettable powder, a granular wettable powder, a flowable, a granule, a dry flowable, an emulsifiable concentrate, a microcapsule, or the others.

Examples of the solid carrier to be used in formulating the Compound A include fine powders and granules of clays (for example, kaolin clay, diatomaceous earth, bentonite, or acid white clay), dry silica, wet silica, talc, ceramic, other inorganic minerals (for example, sericite, quartz, sulfur, active carbon, or calcium carbonate), chemical fertilizers (for example, ammonium sulfate, ammonium phosphate, ammonium nitrate, urea, or ammonium chloride), and the others; as well as synthetic resins (for example, polyester resins such as polypropylene, polyacrylonitrile, polymethylmethacrylate, and polyethylene terephthalate; nylon resins such as nylon-6, nylon-11, and nylon-66; polyamide resins; polyvinyl chloride, polyvinylidene chloride, vinyl chloride-propylene copolymers, or the others).

Examples of the liquid carrier include water; alcohols (for example, methanol or ethanol); ketones (for example, acetone or methyl ethyl ketone); aromatic hydrocarbons (for example, toluene or xylene); aliphatic hydrocarbons (for example, hexane or cyclohexane); esters (for example, ethyl acetate or butyl acetate); nitriles (for example, acetonitrile); ethers (for example, diisopropyl ether or diethylene glycol dimethyl ether); amides (for example, N,N-dimethylformamide); sulfoxides (for example, dimethyl sulfoxide); and vegetable oils (for example, soybean oil or cottonseed oil).

Examples of the surfactant include nonionic surfactants such as polyoxyethylene alkyl ethers, polyoxyethylene alkyl aryl ethers, and polyethylene glycol fatty acid esters; and anionic surfactants such as alkyl sulfonates, alkylbenzene sulfonates, and alkyl sulfates.

Examples of the other auxiliary agent for formulation include binders, dispersants, colorants, and stabilizers. Specific examples thereof include casein, gelatin, saccharides (for example, starch, gum arabic, cellulose derivatives, or alginic acid), lignin derivatives, bentonite, water-soluble synthetic polymers (for example, polyvinyl alcohol, polyvinyl pyrrolidone, or polyacrylic acids), acidic isopropyl phosphate, 2,6-di-tert-butyl-4-methylphenol, and BHA (a mixture of 2-tert-butyl-4-methoxyphenol and 3-tert-butyl-4-methoxyphenol).

The method for controlling a weed of the present invention comprises applying an effective amount of the Compound A to a weed, or a habitat where a weed lives, or a place where a weed would live. In the method for controlling a weed of the present invention, the Compound A is usually used in the form of the Composition A. Examples of the method for controlling a weed of the present invention include a method wherein the Composition A is applied to a weed by foliage treatment, a method wherein the Composition A is applied to a soil surface where a weed lives or would live, a method wherein the Composition A is incorporated into soil where a weed lives, and a method wherein the Composition A is applied to surface water of a paddy field prepared by flooding a place where a weed lives or would live. The amount of the Compound A to be used in the method for controlling a weed of the present invention is usually within the range of 5 to 5000 g per 1 ha of area to be subjected to weed control.

The Compound A may be used in a cropland and the others where a useful plant is cultivated to control weeds in said cropland.

Examples of the above useful plant include corn, rice, wheat, barley, rye, oat, sorghum, cotton, soybean, peanut, beet, rapeseed, sunflower, sugar cane, tobacco, hop;

solanaceous vegetables (for example, eggplant, tomato, pimento, pepper, or potato), cucurbitaceous vegetables (for example, cucumber, pumpkin, zucchini, water melon, melon, or oriental melon), cruciferous vegetables (for example, Japanese radish, white turnip, horseradish, kohlrabi, Chinese cabbage, cabbage, leaf mustard, broccoli, or cauliflower), asteraceous vegetables (for example, burdock, crown daisy, artichoke, or lettuce), liliaceous vegetables (for example, welsh onion, onion, garlic, or asparagus), ammiaceous vegetables (for example, parsley, celery, or parsnip), chenopodiaceous vegetables (for example, spinach or Swiss chard), lamiaceous vegetables (for example, perilla, mint, or basil), leguminous crops (for example, pea, kidney bean, adzuki bean, broad bean, or chick pea), strawberry, sweet potato, glutinous yam, eddoe, Konjac, ginger, okra;

pomaceous fruits (for example, apple, Japanese pear, pear, Chinese quince, or quince), stone fleshy fruits (for example, peach, plum, nectarine, Japanese apricot (Prunus mume), cherry fruit, apricot, or prune), citrus fruits (for example, Citrus unshiu, orange, lemon, lime, or grapefruit), nuts (for example, chestnuts, walnuts, hazelnuts, almond, pistachio, cashew nuts, or macadamia nuts), berry fruits (for example, blueberry, cranberry, blackberry, or raspberry), grapes, Japanese persimmon, olive, Japanese plum, banana, coffee, date palm, coconuts, oil palm, and the others.

The above-mentioned useful plant(s) may include genetically modified plant(s).

Examples of target to be controlled by the Compound A include the followings.

Urticaceae weeds: *Urtica ureas;*

Polygonaceae weeds: *Polygonum convolvulus, Polygonum lapathifolium, Polygonum pensylvanicum, Polygonum persicaria, Polygonum longisetum, Polygonum aviculare, Polygonum arenastrum, Polygonum cuspidatum, Rumex japonicus, Rumex crispus, Rumex obtusifolius,* and *Rumex acetosa;*

Portulaceae weeds: *Portulaca oleracea;* Caryophyllaceae weeds: *Stellaria media, Stellaria aquatica, Cerastium holosteoides, Cerastium glomeratum, Spergula arvensis,* and *Silene gallica;*

Molluginaceae weeds: *Mollugo verticillata;* Chenopodiaceae weeds: *Chenopodium album, Chenopodium ambrosioides, Kochia scoparia, Salsola kali,* and *Atriplex* spp.;

Amaranthaceae weeds: *Amaranthus retroflexus, Amaranthus viridis, Amaranthus lividus, Amaranthus spinosus, Amaranthus hybridus, Amaranthus palmeri, Amaranthus patulus, Amaranthus tuberculatus, Amaranthus blitoides, Amaranthus deflexus, Amaranthus quitensis, Alternanthera philoxeroides, Alternanthera sessilis,* and *Alternanthera tenella;*

Papaveraceae weeds: *Papaver rhoeas, Papaver dubium,* and *Argemone mexicana;*

Brassicaceae weeds: *Raphanus raphanistrum, Raphanus sativus, Sinapis arvensis, Capsella bursa-pasto Brassica juncea, Brassica napus, Descurainia pinnata, Rorippa islandica, Rorippa sylvestris, Thlaspi arvense, Myagrum rugosum, Lepidium virginicum,* and *Coronopus didymus;*

Capparaceae weeds: *Cleome affinis;*

Fabaceae weeds: *Aeschynomene indica, Aeschynomene rudis, Sesbania exaltata, Cassia obtusifolia, Cassia occidentalis, Desmodium tortuosum, Desmodium adscendens, Desmodium illinoense, Trifolium repens, Pueraria lobata, Vicia angustifolia, Indigofera hirsuta, Indigofera truxillensis,* and *Vigna sinensis;*

Oxalidaceae weeds: *Oxalis corniculata, Oxalis strica,* and *Oxalis oxyptera;*

Geraniaceae weeds: *Geranium carolinense* and *Erodium cicutarium;*

Euphorbiaceae weeds: *Euphorbia helioscopia, Euphorbia maculata, Euphorbia humistrata, Euphorbia esula, Euphorbia heterophylla, Euphorbia brasiliensis, Acalypha australis, Croton glandulosus, Croton lobatus, Phyllanthus corcovadensis,* and *Ricinus communis;*

Malvaceae weeds: *Abutilon theophrasti, Sida rhombifolia, Sida cordifolia, Side spinosa, Side glaziovii, Sida santaremnensis, Hibiscus trionum, Anoda cristata,* and *Malvastrum coromandelianum;*

Onagraceae weeds: *Ludwigia epilobioides, Ludwigia octovalvis, Ludwigia decurre, Oenothera biennis,* and *Oenothera laciniata;*

Sterculiaceae weeds: *Waitheria indica;*

Violaceae weeds: *Viola arvensis* and *Viola tricolor;*

Cucurbitaceae weeds: *Sicyos angulatus, Echinocystis lobata,* and *Mornordica charantia;*

Lythraceae weeds: *Ammannia multiflora, Ammannia auriculata, Ammannia coccinea, Lythrum salicaria,* and *Rotala indica;*

Elatinaceae weeds: *Elatine triandra* and *Elatine californica;*

Apiaceae weeds: *Qenanthe javanica*, *Daucus carota*, and *Conium maculatum*;

Araliaceae weeds: *Hydrocotyle sibthorpioides* and *Hydrocotyle ranunculoides*;

Ceratophyllaceae weeds: *Ceratophyllum demersum*;

Cabombaceae weeds: *Cabomba caroliniana*;

Haloragaceae weeds: *Myriophyllum aquaticum*, *Myriophyllum verticillatum*, and watermilfoils (for example, *Myriophyllum spicatum* and *Myriophyllum heterophyllum*);

Sapindaceae weeds: *Cardiospermum halicacabum*;

Primulaceae weeds: *Anagallis arvensis*;

Asclepiadaceae weeds: *Asclepias syriaca* and *Ampelamus albidus*;

Rubiaceae weeds: *Galium aparine*, *Galium spurium* var. *echinospermon*, *Spermacoce latifolia*, *Richardia brasiliensis*, and *Borreria alata*;

Convolvulaceae weeds: *Ipomoea nil*, *Ipomoea hederacea*, *Ipomoea purpurea*, *Ipomoea hederacea* var. *integriuscula*, *Ipomoea lacunosa*, *Ipomoea triloba*, *Ipomoea acuminata*, *Ipomoea hederifolia*, *Ipomoea coccinea*, *Ipomoea quamoclit*, *Ipomoea grandifolia*, *Ipomoea aristolochiafolia*, *Ipomoea cairica*, *Convolvulus arvensis*, *Calystegia hederacea*, *Calystegia japonica*, *Merremia hedeacea*, *Merremia aegyptia*, *Merremia cissoides*, and *Jacquemontia tamnifolia*;

Boraginaceae weeds: *Myosotis arvensis*;

Lamiaceae weeds: *Lamium purpureum*, *Lamium amplexicaule*, *Leonotis nepetaefolia*, *Hyptis suaveolens*, *Hyptis lophanta*, *Leonurus sibiricus*, and *Stachys arvensis*;

Solanaceae weeds: *Datura stramonium*, *Solanum nigrum*, *Solanum americanum*, *Solanum ptycanthum*, *Solanum sarrachoides*, *Solanum rostratum*, *Solanum aculeatissimum*, *Solanum sisymbrilfolium*, *Solanum carolinense*, *Physalis angulata*, *Physalis subglabrata*, and Nicandra physaloides;

Scrophulariaceae weeds: *Veronica hederaefolia*, *Veronica persica*, *Veronica arvensis*, *Lindernia procumbens*, *Lindernia dubia*, *Lindernia angustifolia*, *Bacopa rotundifolia*, *Dopatrium junceum*, and *Gratiola japonica*;

Plantaginaceae weeds: *Plantago asiatica*, *Plantago lanceolata*, *Plantago major*, and *Callitriche palustris*;

Asteraceae weeds: *Xanthium pensylvanicum*, *Xanthium occidentale*, *Xanthium italicum*, *Helianthus annuus*, *Matricaria chamomilla*, *Matricaria perforata*, *Chrysanthemum segetum*, *Matricaria matricarioides*, *Artemisia princeps*, *Artemisia vulgaris*, *Artemisia verlotorum*, *Solidago altissima*, *Taraxacum officinale*, *Galinsoga ciliata*, *Galinsoga parviflora*, *Senecio vulgaris*, *Senecio brasiliensis*, *Senecio grisebachii*, *Conyza bonariensis*, *Conyza smatrensis*, *Conyza canadensis*, *Ambrosia artemisiaefolia*, *Ambrosia trifida*, *Bidens tripartite*, *Bidens pilosa*, *Bidens frondosa*, *Bidens subalternans*, *Cirsium arvense*, *Cirsium vulgare*, *Silybum marianum*, *Carduus nutans*, *Lactuca serriola*, *Sonchus oleraceus*, *Sonchus aspen*, *Wedelia glauca*, *Melampodium perfoliatum*, *Emilia sonchifolia*, *Tagetes minuta*, *Blainvillea latfolia*, *Tridax procumbens*, *Porophyllum ruderale*, *Acanthospermum australe*, *Acanthospermum hispidum*, *Cardiospermum halicacabum*, *Ageratum conyzoides*, *Eupatorium perfoliatum*, *Eclipta alba*, *Erechtites hieracifolia*, *Gamochaeta spicata*, *Gnaphalium spicatum*, *Jaegeria hirta*, *Parthenium hysterophorus*, *Siegesbeckia orientalis*, *Soliva sessilis*, *Eclipta prostrata*, *Eclipta alba*, and *Centipeda minima*;

Alismataceae weeds: *Sagittaria pygmaea*, *Sagittaria trifolia*, *Sagittaria sagittifolia*, *Sagittaria montevidensis*, *Sagittaria aginashi*, *Alisma canaliculatum*, and *Alisma plantago-aquatica*;

Limnocharitaceae weeds: *Limnocharis flava*;

Hydrocharitaceae weeds: *Limnobium spongia*, *Hydrilla verticillata*, and *Najas guadalupensis*;

Araceae weeds: *Pistia stratiotes*;

Lemnaceae weeds: *Lemna aoukikusa*, *Spirodela polyrhiza*, and *Wolffia* spp.;

Potamogetonaceae weeds: *Potamogeton distinctus* and pondweeds (for example, *Potamogeton crispus*, *Potamogeton illinoensis*, and *Stuckenia pectinate*);

Liliaceae weeds: *Allium canadense*, *Allium vineale*, and *Allium macrostemon*;

Pontederiaceae weeds: *Eichhornia crassipes*, *Heteranthera limosa*, *Monochoria korsakowii*, and *Monochoria vaginalis*;

Commelinaceae weeds: *Commelina communis*, *Commelina bengharensis*, *Commelina erecta*, and *Murdannia keisak*;

Poaceae weeds: *Echinochloa crus-Balli*, *Echinochloa oryzicola*, *Echinochloa crus-galli* var. *formosensis*, *Echinochloa oryzoides*, *Echinochloa colona*, *Echinochloa cruspavonis*, *Setaria viridis*, *Setaria faberi*, *Setaria glauca*, *Setaria geniculata*, *Digitaria ciliaris*, *Digitaria sanguinalis*, *Digitaria horizontalis*, *Digitaria insularis*, *Eleusine indica*, *Poa annua*, *Poa trivialis*, *Poa pratensis*, *Alospecurus aequalis*, *Alopecurus myosuroides*, *Avena fatua*, *Sorghum halepense*, *Sorghum vulgare*, *Agropyron repens*, *Lolium multiflorum*, *Lolium perenne*, *Lolium rigidum*, *Bromus catharticus*, *Bromus sterilis*, *Bromus japonicus*, *Bromus secalinus*, *Bromus tectorum*, *Hordeum jubatum*, *Aegilops cylindrica*, *Phalaris arundinacea*, *Phalaris minor*, *Apera Spica-venti*, *Panicum dichotomiflorum*, *Panicum texanum*, *Panicum maximum*, *Brachiaria platyphylla*, *Brachiaria ruzienss*, *Brachiaria plantaginea*, *Brachiaria decumbens*, *Brachiaria brizantha*, *Brachiaria humidicola*, *Cenchrus echinatus*, *Cenchrus pauciflorus*, *Eriochloa villosa*, *Pennisetum setosum*, *Chloris gavana*, *Chloris virgata*, *Eragrostis pilosa*, *Rhynchelitrum repens*, *Dactyloctenium aegyptium*, *Ischaemum rugosum*, *Isachne globosa*, *Oryza sativa*, *Paspalum notatum*, *Paspalum maritimum*, *Paspalum distichum*, *Pennisetum clandestinum*, *Pennisetum setosum*, *Rottboellia cochinchinensis*, *Leptochloa chinensis*, *Leptochloa fascicularis*, *Leptochloa filiformis*, *Leptochloa panicoides*, *Leersia japonica*, *Leersia sayanuka*, *Leersia oryzoides*, *Glyceria leptorrhiza*, *Glyceria acutiflora*, *Glyceria maxima*, *Agrostis gigantea*, *Agrostis stolonifera*, *Cynodon dactylon*, *Dactylis glomerata*, *Eremochloa ophiuroides*, *Festuca arundinacea*, *Festuca rubra*, *Imperata cylindrica*, *Miscanthus sinensis*, *Panicum virgatum*, and *Zoysia japonica*;

Cyperaceae weeds: *Cyperus microiria*, *Cyperus iria*, *Cyperus compressus*, *Cyperus difformis*, *Cyperus flaccidus*, *Cyperus globosus*, *Cyperus nipponics*, *Cyperus odoratus*, *Cyperus serotinas*, *Cyperus rotundus*, *Cyperus esculentus*, *Kyllinga gracillima*, *Kyllinga brevifolia*, *Fimbristylis miliacea*, *Fimbristylis dichotoma*, *Eleocharis acicularis*, *Eleocharis kuroguwai*, *Schoenoplectiella hotarui*, *Schoenoplectiella juncoides*, *Schoenoplectiella wallichii*, *Schoenoplectiella mucronatus*, *Schoenoplectiella triangulates*, *Schoenoplectiella nipponicus*, *Schoenoplectiella triqueter*, *Bolboschoenus koshevnikovii*, and *Bolboschoenus fluviatilis*;

Equisetaceae weeds: *Equisetum arvense* and *Equisetum palustre*;

Salviniaceae weeds: *Salvinia natans*;

Azollaceae weeds: *Azolla japonica* and *Azolla imbricata*;

Marsileaceae weeds: *Marsilea quadrifolia*;

Others: filamentous algae (for example, Pithophora and Cladophora), moss, liverwort, hornwort, cyanobacteria, fern, and suckers of perennial crops (for example, pomaceous fruits, drupe fruits, berry fruits, nuts, citrus fruits, hop, and grapes);

and the others.

EXAMPLES

The following Examples including Preparation Examples, Formulation Examples, and Test Examples, serve to illustrate the present invention in more detail, which should not intend to limit the present invention.

First, a Preparation Example of the Compound A is described. The Compound B used in the Preparation Example is disclosed in U.S. Pat. No. 6,537,948 B1 as Present Compound 7-8, and may be prepared according to, for example, a method described in Production Example 23 of U.S. Pat. No. 6,537,948 B1.

Step 1

To a solution of Compound B (10 g) and chloroform (40 g) was added meta-chloroperbenzoic acid (hereinafter referred to as "mCPBA") (4.7 g), and the resulting mixture was stirred at 60° C. for 2 hours. To the solution was further added mCPBA (4.7 g), the resulting mixture was stirred at 60° C. for 2 hours, mCPBA (4.7 g) was further added thereto, and the resulting mixture was stirred at 60° C. for 3 hours. The resulting mixture was cooled to room temperature, and washed sequentially with a saturated aqueous solution of sodium sulfite, a 5% aqueous solution of sodium carbonate, and water. The resulting organic layer was concentrated under reduced pressure. The resulting residue was purified by silica gel column chromatography to give Intermediate A (2.05 g) represented by the following formula.

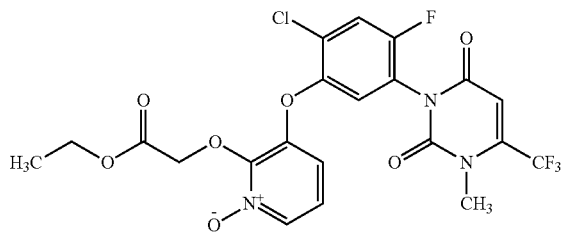 [SMILES: CCOC(=O)COc1c(Oc2cc(-n3c(=O)cc(C(F)(F)F)n(C)c3=O)c(F)cc2Cl)ccc[n+]1O]

Intermediate A: $^1$H-NMR (CDCl$_3$) δ (ppm): 1.25 (3H, t), 3.54 (3H, s), 4.18 (2H, q), 5.23 (1H, d), 5.35 (1H, d), 6.33 (1H, s), 6.85-6.96 (2H, m), 7.06 (1H, d), 7.41 (1H, d), 7.94 (1H, dd).

Step 2

To a solution of Intermediate A (298 mg) and chloroform (3.27 g) were sequentially added 1-methyl-6-(trifluoromethyl)uracil (220 mg), diisopropylethylamine (0.315 mL), and tosyl chloride (129 mg) under ice-cooling, and the resulting mixture was stirred under ice-cooling for 6 hours. The resulting mixture was warmed to room temperature, and stirred for 18 hours. To the resulting mixture was added water (3 mL), and the resulting mixture was separated. The resulting organic layer was dried over anhydrous magnesium sulfate, and concentrated under reduced pressure. The resulting residue was purified by silica gel column chromatography to give Compound A (101 mg).

The $^1$H-NMR data of Compound A is shown below.

$^1$H-NMR (CD$_3$CN) δ (ppm): 1.16 (3H, t), 3.428 (3H, s), 3.432 (3H, s), 4.11 (2H, q), 4.81 (2H, s), 6.32 (1H, s), 6.34 (1H, s), 6.95 (1H, d), 7.11 (1H, d), 7.43 (1H, d), 7.58 (1H, d).

Next, Formulation Examples of Compound A are shown below. In the Formulation Examples, the "part(s)" represents "part(s) by weight".

Formulation Example 1

Compound A (5 parts), GERONOL (registered trademark) FF/4-E (2 parts), GERONOL (registered trademark) FF/6-E (8 parts), and SOLVESSO (registered trademark) 200 (85 parts) are fully mixed to obtain a formulation.

Formulation Example 2

To Compound A (1.5 parts) are added sodium ligninsulfonate (2 parts), talc (40 parts), and bentonite (56.5 parts), followed by mixing them to obtain a mixture. To the mixture is then added an appropriate amount of water, the resulting mixture is additionally stirred, and subjected to granulation with a granulator and forced-air drying to obtain a formulation.

Formulation Example 3

A mixture of polyoxyethylene alkyl ether sulfate ammonium salt and wet silica (weight ratio 1:1) (35 parts), Compound A (10 parts), and water (55 parts) are fully mixed to obtain a formulation.

Next, weed control efficacies of the Compound A and safety (phytotoxicity) of the Compound A against a useful plant are shown by a Test Example. In the following Test Example, a group where the status of budding or growth of the test plant at the time of the investigation is the same or substantially the same as that in the untreated group is set to be "0" and a group where the test plant is completely dead or the budding or growth is completely inhibited is set to be "100" to evaluate the weed control efficacies by a score of 0 to 100.

Here the "untreated group" represents a group where the same treatment procedure as that of the treated group except not using the Compound A is done.

Test Example 1

A plastic pot was filled with soil, thereto *Amaranthus retroflexus, Ipomoea hederacea*, and corn were seeded, and they were grown in a greenhouse for 15 days. Separately, a prescribed amount of a formulation prepared according to the process described in the Formulation Example 1 was diluted with water comprising 1% of Agridex (registered trademark) to obtain a diluent. Said diluent was homogeneously sprayed from above of said plants in a ratio of 204 L/ha such that the applied amount of the Compound A was 80 gai/ha or 40 gai/ha. Then, said plants were grown in a greenhouse for 11 days and evaluated according to the above criteria. The results are shown in Table 1.

TABLE 1

| Applied amount [gai/ha] | Amaranthus retroflexus | Ipomoea hederacea | Corn |
|---|---|---|---|
| 80 | 100 | 100 | 10 |
| 40 | 100 | 95 | 5 |

The Compound A showed high weed control efficacies against *Amaranthus retroflexus* and *Ipomoea hederacea*.

Further, the Compound A showed low phytotoxicity against corn, and thus showed high safety against the useful plant.

Comparative Example 1

The Compound B was used instead of the Compound A to carry out the same test as the Test Example 1. The results are shown in Table 2.

TABLE 2

| Applied amount [gai/ha] | *Amaranthus retroflexus* | *Ipomoea hederacea* | corn |
|---|---|---|---|
| 80 | 100 | 100 | 100 |
| 40 | 100 | 100 | 100 |

The Compound B showed not only high weed control efficacies against *Amaranthus retroflexus* and *Ipomoea hederacea*, but also high phytotoxicity against a useful plant, corn.

INDUSTRIAL APPLICABILITY

The Compound A has excellent control efficacies against weeds and high safety against useful plants, and thus is useful as an active ingredient of a herbicidal composition.

The invention claimed is:

1. A compound represented by formula (A)

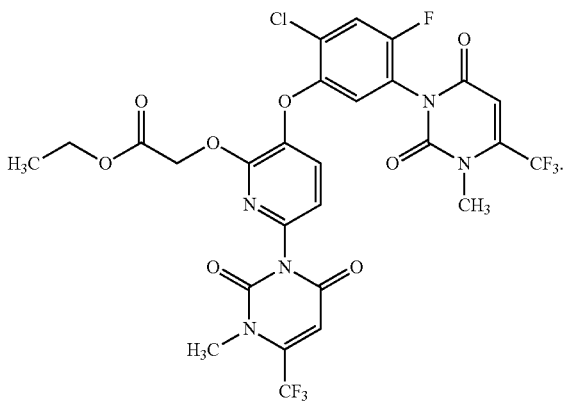

2. A herbicidal composition comprising the compound according to claim 1 and an inert carrier.

3. A method for controlling a weed which comprises applying the compound according to claim 1 to a weed or a habitat where a weed lives.

* * * * *